US009089512B2

(12) United States Patent
Mooney et al.

(10) Patent No.: US 9,089,512 B2
(45) Date of Patent: Jul. 28, 2015

(54) ACTIVE SCAFFOLDS FOR ON-DEMAND DRUG AND CELL DELIVERY

(75) Inventors: David J. Mooney, Sudbury, MA (US); Xuanhe Zhao, Durham, NC (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 13/516,973

(22) PCT Filed: Dec. 15, 2010

(86) PCT No.: PCT/US2010/060456
§ 371 (c)(1),
(2), (4) Date: Aug. 22, 2012

(87) PCT Pub. No.: WO2011/075516
PCT Pub. Date: Jun. 23, 2011

(65) Prior Publication Data
US 2013/0017229 A1    Jan. 17, 2013

Related U.S. Application Data

(60) Provisional application No. 61/288,028, filed on Dec. 18, 2009.

(51) Int. Cl.
| | |
|---|---|
| *A61K 38/08* | (2006.01) |
| *A61K 9/00* | (2006.01) |
| *A61K 9/06* | (2006.01) |
| *A61K 9/50* | (2006.01) |
| *A61K 38/06* | (2006.01) |
| *A61K 47/36* | (2006.01) |
| *A61K 47/48* | (2006.01) |
| *A61L 27/38* | (2006.01) |
| *A61L 27/44* | (2006.01) |
| *A61L 27/50* | (2006.01) |
| *A61L 27/54* | (2006.01) |
| *A61L 27/56* | (2006.01) |
| *A61K 41/00* | (2006.01) |

(52) U.S. Cl.
CPC ............... *A61K 38/08* (2013.01); *A61K 9/0009* (2013.01); *A61K 9/0024* (2013.01); *A61K 9/06* (2013.01); *A61K 38/06* (2013.01); *A61K 41/0028* (2013.01); *A61K 47/36* (2013.01); *A61K 47/48238* (2013.01); *A61K 47/48784* (2013.01); *A61L 27/3804* (2013.01); *A61L 27/446* (2013.01); *A61L 27/50* (2013.01); *A61L 27/54* (2013.01); *A61L 27/56* (2013.01); *A61K 9/5094* (2013.01); *A61L 2300/602* (2013.01)

(58) Field of Classification Search
CPC ....... A61K 9/0009; A61K 9/06; A61K 38/06; A61K 38/08; A61K 41/0028; A61K 47/36; A61K 47/48238; A61K 47/48784; A61K 9/0024; A61K 9/5094; A61L 27/3804; A61L 27/446; A61L 27/50; A61L 27/54; A61L 27/56; A61L 2300/602

USPC .......... 424/400, 93.7, 469, 489, 501; 514/653, 514/965
See application file for complete search history.

(56) References Cited

U.S. PATENT DOCUMENTS

| | | | |
|---|---|---|---|
| 5,714,536 | A | 2/1998 | Ziolo et al. |
| 2004/0028745 | A1 * | 2/2004 | Bouhadir et al. ............. 424/488 |
| 2007/0141339 | A1 * | 6/2007 | Song et al. .................... 428/402 |
| 2009/0053512 | A1 | 2/2009 | Pyun et al. |

FOREIGN PATENT DOCUMENTS

| | | |
|---|---|---|
| WO | 0172281 A2 | 10/2001 |
| WO | WO 01/72281 A2 * | 10/2001 |
| WO | 2006/116752 A2 | 11/2006 |
| WO | 2007/065933 A1 | 6/2007 |
| WO | 2011/086210 A1 | 7/2011 |

OTHER PUBLICATIONS

Bueche et al., Journal of Applied Physics, 35(1):36-41 (1964). "Molecular Theory for the Tensile Strength of Gum Elastomers."
Caykara et al., Journal of Applied Polymer Science, 112:800-804 (2009). "Preparation and Characterization of Poly (N-tert-butylacrylamide-co-acrylamide) Ferrogel."
Chatterjee et al., Colloid Polym Sci, 281:892-896 (2003). "Biodegradable magnetic gel: synthesis and characterization."
Dainiak et al., PNAS, 103(4):849-854 (2006). "Detachment of Affinity-Captured Bioparticles by Elastic Deformation of a Macroporous Hydrogel."
Gu et al., Colloid Polym Sci, 281:1076-1081 (2003). "Synthesis of monodisperse, magnetic latex particles with polystyrene core."
Hu et al., Journal of Controlled Release, 121:181-189 (2007). "Nano-ferrosponges for controlled drug release."
Hu et al., Macromolecules, 40:6786-6788 (2007). "Controlled Pulsatile Drug Release from a Ferrogel by a High-Frequency Magnetic Field."
Hu et al., Adv. Mater., 20:2690-2695 (2008). "Core/Single-Crystal-Shell Nanospheres for Controlled Drug Release via a Magnetically Triggered Rupturing Mechanism."
Lee et al., Nature, 408:998-1000 (2000). "Controlled growth factor release from synthetic extracellular matrices."
Liu et al., Langmuir, 22:5974-5978 (2006). "Magnetic-Sensitive Behavior of Intelligent Ferrogels for Controlled Release of Drug."
Lu et al., Nature, 410:913-917 (2001). "Self-assembly of mesoscopically ordered chromatic polydiacetylene/silica nanocomposites."

(Continued)

*Primary Examiner* — Blessing M Fubara
(74) *Attorney, Agent, or Firm* — Nixon Peabody LLP (57) ABSTRACT

The invention provides a composition whose porosity, pore size, pore connectivity, swelling agent concentration, and/or specific volume undergoes a change from a first value to a second value in response to an electromagnetic signal, the composition having a matrix material in which is distributed a magnetic material.

23 Claims, 3 Drawing Sheets

(56) References Cited

OTHER PUBLICATIONS

Lu et al., Langmuir, 21:2042-2050 (2005). "Magnetic Switch of Permeability for Polyelectrolyte Microcapsules Embedded with Co@Au Nanoparticles."

Qin et al., Adv. Mater. 21:1354-1357 (2009). "Injectable Superparamagnetic Ferrogels for Controlled Release of Hydrophobic Drugs."

Resendiz-Hernandez et al., Journal of Magnetism and Magnetic Materials, 320:e373-e376 (2008). "Synthesis of poly(vinyl alcohol)-magnetite ferrogel obtained by freezing-thawing technique."

Rowley et al., Biomaterials, 20:45-53 (1999). "Alginate hydrogels as synthetic extracellular matrix materials."

Sahiner et al., Colloid Polym Sci., 284:1121-1129 (2006). "Microgel, nanogel and hydrogel-hydrogel semi-IPN composites for biomedical applications: synthesis and characterization."

Sauzedde et al., Colloid Polym Sci., 277:846-855 (1999). "Hydrophilic magnetic polymer latexes. 1. Adsorption of magnetic iron oxide nanoparticles onto various cationic latexes."

Zhang et al., Adv. Mater. 14(23):1756-1759 (2002). "A New Approach to Hybrid Polymer-Metal and Polymer-Semiconductor Particles."

Zrinyi et al., J. Chem. Phys., 104(21):8750-8756 (1996). "Deformation of ferrogels induced by nonuniform magnetic fields."

Zrinyi et al., Polymer Gels and Networks, 5:415-427 (1997). "Ferrogel: a new magneto-controlled elastic medium."

\* cited by examiner

ACTIVE SCAFFOLDS FOR ON-DEMAND DRUG AND CELL DELIVERY

CROSS REFERENCE TO RELATED APPLICATIONS

This application is a 35 U.S.C. §371 National Stage Entry Application of International Application No. PCT/US2010/060456, filed Dec. 15, 2010, which designates the U.S., and which claims benefit under 35 U.S.C. §119(e) of the U.S. Provisional Application No. 61/288,028, filed Dec. 18, 2009, the content of which is incorporated herein by reference in its entirety.

GOVERNMENT SUPPORT

This invention was made with government support under grant no. DMR-0820484 awarded by the National Science Foundation and under grant no. DE013033 awarded by the National Institutes of Health. The government has certain rights in this invention.

FIELD OF THE INVENTION

The invention relates to materials that can vary their porosity, pore size, pore connectivity, swelling agent concentration, and/or specific volume in response to an external stimuli. This invention further relates to use of these materials for control release drug and cell delivery.

BACKGROUND OF THE INVENTION

Stimuli-responsive polymers represent one class of actuators that have the unique ability to change swelling behaviors, permeability, and elasticity in a reversible manner. Owing to these useful properties, stimuli-responsive polymers have numerous applications, particularly in medicine, pharmaceutics, drug-delivery, biosensors, separation and membranes, purifications, and enzyme and cell immobilization (Qiu, Y. and Park, K. Adv Drug Delivery Rev (2001), 53: 321-339; Miyata, T. Urgami, T. and Nakamae, K. Adv. Drug Delivery Rev. (2002), 54: 79-98; Bckiari, V. et al., Langmuir (2004), 20: 7972; Lopes, D. Cendoya, L. and Mijangos, C. Macromol Symp (2001), 166:173; Lao, L. and Ramanujan, V. R. J Mater Sci Mater Med (2004), 15: 1061; Porter, J. and Pickup, R. W. J. Microbiol. Methods (1998), 33: 221; Xie, X. et al., J Magn Mater (2004), 227: 16 and Gupta, P. K. and Hung, C. T. Life Sci (19889) 44, 175).

Magnetic gels, also called ferrogels, are a class of stimuli-responsive polymeric materials with their properties controlled by magnetic field. Ferrogels contain magnetic particles dispersed homogenously or heterogeneously and confined in a polymer network. Under a non-uniform magnetic field, particles undergo motion, which in turn induces elongation, contraction, or bending of the gels with short response time (Torok, G. et al., Phys B (2001) 297: 40; Szabo, D. Czako-Nagu, I. and Zrinyi, M. J Colloid Interface Sci (2002) 221: 166; Szabo, D. Szeghy, G. and Zrinyi, M. Macromolecules (1998) 31: 6541; Xulu, P. Filipesei, G. and Zrinyi, M. Macromolecules (2000) 33: 1716; Zrinyi, M. Feher, J. and Filipesei, G. Macromolecules (2000) 33: 5751; Zrinyi, M. Barsi, L. and Buki, A. J Chem Phys (1996) 104: 8750; and Zrinyi, M. Barsi, L. and Buki, A. Polym Gels Networks (1997) δ: 415). Although magnetic gels under go changes with short response time, these changes, especially changes in specific volume, are not substantial.

It would be desirable to have materials that can undergo substantial specific volume changes in response to an external stimuli.

SUMMARY OF THE INVENTION

In one aspect, the invention provides a composition comprising a matrix material and a magnetic material distributed therethrough, wherein the composition comprises pores having mean pore diameter in range of about 100 μm to about 1000 μm, and wherein porosity, pore size, pore connectivity, swelling agent concentration and/or specific volume of the composition undergoes a change from a first value to a second value in response to an electromagnetic signal.

In another aspect, the invention provides a method for releasing a therapeutic agent on demand in response to an external stimuli, the method comprising: (a) providing to a subject a composition described herein, wherein the composition contains the therapeutic agent; and (b) inducing a change in porosity, pore size, pore connectivity, swelling agent concentration, and/or specific volume of the composition via a magnetic field to release the drug.

BRIEF DESCRIPTION OF THE DRAWINGS

The patent or application file contains at least one drawing executed in color. Copies of this patent or patent application publication with color drawing(s) will be provided by the United States Patent and Trademark Office upon request and payment of the necessary fees.

FIGS. 3A-3D shows effect of a magnetic field on the compositions described herein. In absence of magnetic field, the pores in the gel have spherical shapes with diameter ~700 μm, and are highly connected (FIG. 3A). When the magnetic field is applied, the pores deform into slits with heights ~30 μm, and the connectivity between pores becomes poor (FIG. 3B). A large amount of cells migrate out of the gel with magnetic field off (FIG. 3C) On the other hand, if the magnetic field is on, very few cells can migrate out of the gel (FIG. 3B). Cells might be seeded in the macroporous gels for migration and proliferation.

DETAILED DESCRIPTION OF THE INVENTION

In one aspect, the invention provides a composition comprising a matrix material and a magnetic material distributed therethrough, wherein the composition comprises pores having mean pore diameter in range of about 100 μm to about 1000 μm, and wherein porosity, pore size, pore connectivity, swelling agent concentration and/or specific volume of the composition undergoes a change from a first value to a second value in response to an electromagnetic signal. It is to be understood that, change in one of porosity, pore size, pore connectivity, swelling agent concentration, and/or specific volume can be independent of change in one of the others, i.e., change in one may or may not effect a change in others.

Ratio of matrix to magnetic material in the composition can range from about 1:20 (matrix:magnetic) to about 20:1. The ratio can be in the range of from about 1:120 to about 10:1, from about 1:30 to about 5:1, or from about 1:20 to about 1:1. In some embodiments, the ratio is in the range of about 1:20 to about 1:5. In some embodiments, the ratio is around 1:13. In one preferred embodiment, the ratio is in the range from about 1:1 to about 3:1. It is to be understood that ratio can be based on weight, volume and/or moles.

A composition described herein can comprise any amount of matrix and magnetic materials. For example, the composition can comprise 0.1-50% of the matrix material and 10-99% of the magnetic material. In some embodiments, the composition comprises 1-25% of the matrix material and 75-99% of the magnetic material. Preferably, the composition comprises 1-20% of the matrix material and 80-90% of the magnetic material. In some even more preferred embodiments, the composition comprises 1-15% of the matrix material and 85-99% of the magnetic material. In one most preferred embodiment, the composition comprises 5-10% of the matrix material and 90-95% of the magnetic material. The percent values can be based on weight, volume and/or moles. In addition to the matrix and the magnetic materials, the composition can comprise additional substances such as a swelling agent. When an additional substance is present in the composition, matrix and magnetic material percent values are calculated based on the matrix and magnetic material only.

Alternatively, composition can comprise 0.1%-50% of matrix material, 1-90% of magnetic material and a swelling agent in an amount corresponding to the balance up to 100%. Again percent values can be based on weight, volume and/or moles. In one embodiments, percent values are based on weight. In some embodiments, the composition comprises 0.1%-25% of matrix material, 5-50% of magnetic material and a swelling agent in an amount corresponding to the balance up to 100%. In some other embodiments, the composition comprises 0.1%-25% of matrix material, 10-50% of magnetic material and a swelling agent in an amount corresponding to the balance up to 100%. In some embodiments, the composition comprises 0.1%-10% of matrix material, 10-50% of magnetic material and a swelling agent in an amount corresponding to the balance up to 100%. In one embodiment, the composition comprises about 1% matrix, about 13% magnetic material and a swelling agent in an amount corresponding to the balance up to 100%.

The electromagnetic signal generator can include an electromagnet or electrically-polarizable element, or at least one permanent magnet. The electromagnetic signal can be produced at least in part according to a pre-programmed pattern. The electromagnetic signal may have a defined magnetic field strength or spatial orientation, or a defined electric field strength or spatial orientation. In some embodiments, the electromagnetic signal has a defined magnetic field strength. As used herein, the term "magnetic field" refers to magnetic influences which create a local magnetic flux that flows through the composition and can refer to field amplitude, squared-amplitude, or time-averaged squared-amplitude. It is to be understood that magnetic field can be a direct-current (DC) magnetic field or alternating-current (AC) magnetic field. Magnetic field strength can range from about 0.001 Tesla to about 1 Tesla. In some embodiments, magnetic field strength is in the range from about 0.01 Tesla to about 1 Tesla. In some other embodiments, magnetic field strength is in the range from about 0.1 Tesla to about 1 Tesla. Typically, the magnetic field strength is 0.5 Tesla.

In certain embodiments, the composition is macroporous. As used herein, the term "macroporous" refers to the fact that composition comprises macropores. The composition can also comprise micropores. Generally, micropores are pores having a diameter on the order of about 50 Angstroms or less, while macropores are pores having a diameter on the order of about 100 Angstroms or greater. Generally, diameter of a pore is such as to allow free flow of swelling agent and/or a solvent through the pores. Typically, pore diameters of compositions described herein can range from about 0.01 μm to 1000 μm. In some embodiments, the composition comprises pores having mean pore diameter in range from about 150 μm to 1000 μm. In some embodiments, the composition comprises pores having mean pore diameter of 200-750 μm. In one preferred embodiment, the composition comprises pores having mean pore diameter of 250-700 μm. In another preferred embodiment, the composition comprises pores having mean pore diameter of 500-700 μm. In one embodiment, the composition comprises pores having mean pore diameter of around 700 μm.

The changes in porosity, pore size, pore connectivity, swelling agent concentration, and/or specific volume are preferably reversible (i.e., porosity, pore size, pore connectivity, swelling agent concentration, and/or specific volume detectably increases or decreases upon application of the stimuli, and then reverts to its original value, e.g., within 10%, 5%, 2%, 1% or less of the original value, when the stimuli is discontinued). However, it will be recognized that in some applications, reversibility of one or more of porosity, pore size, pore connectivity, swelling agent concentration, and/or specific volume is not essential. The change in specific volume is also referred to as a volume phase transition herein.

It is to be understood that external stimuli can be applied by providing a stimuli that is not present, by holding back a stimuli that is already present, or by changing the amount of a stimuli that is already present.

In some embodiments, in response to an electromagnetic signal, porosity, pore size, pore connectivity, swelling agent concentration, and/or specific volume changes by at least 10%, 15%, 20%, 25% 30%, 40%, 50%, 60%, 70%, 80%, 90%, 95%, 96%, 97%, 98%, 99% or more relative to the original value. In some embodiments, in response to an electromagnetic signal, porosity, pore size, pore connectivity, swelling agent concentration, and/or specific volume changes by at least 70% or more relative to the original value. Preferably, the porosity, pore size, pore connectivity, swelling agent concentration, and/or specific volume decreases in response to the electromagnetic signal.

As used herein, the term "porosity" means the fractional volume (dimension-less) of the composition that is composed of open space, e.g., pores or other openings. See for example, Coulson J. M., et. al., Chemical Engineering (1978), volume 2, $3^{rd}$ Edition, Pergamon Press, 1978, page 126). Generally, in the absence of an external electromagnetic signal, porosity of the composition can range from 0.5 to 0.99. Preferably porosity is in the range of from about 0.75 to about 0.99, more preferably from about 0.8 to about 0.95. Preferably, porosity of the porous material is at least 0.75, more preferably at least 0.8, and most preferably at least 0.9.

Several methods can be employed to measure porosity, including, direct methods (e.g. determining the bulk volume of the porous sample, and then determining the volume of the skeletal material with no pores (pore volume=total volume–material volume), optical methods (e.g., determining the area of the material versus the area of the pores visible under the microscope, where the areal and volumetric porosities are equal for porous media with random structure), imbibition methods (e.g., immersion of the porous sample, under vacuum, in a fluid that preferentially wets the pores), water saturation method (e.g., pore volume=total volume of water−volume of water left after soaking), water evaporation method (e.g., pore volume in cubic centimeters=weight of saturated sample in grams−weight of dried sample in grams), and gas expansion methods. Methods for measuring porosity of a sample are described in Glasbey, C. A. Horgan, G. W. and Darbyshire, J. F. J Soil Sci (1991) 42: 479-486, contents of which are herein incorporated by reference in their entirety.

In some embodiments, the composition is a particle, e.g. a nanoparticle or microparticle. The composition particle size will vary depending on the particular use intended for such a particle. In general, particles can have at least one dimension in the range from about 1000 μm to about 2000 μm. The mass median particle size will generally be from about 1200 to about 1500 μm.

Preparation of compositions described herein does not require a special type of matrix and/or magnetic materials. Any material that comprises a spatial network structure can be used for the matrix. The matrix can comprise materials of synthetic or natural origin (e.g., biopolymers) or a mixture thereof cross-linked by physical and/or chemical interactions. In some embodiments, the matrix is not biodegradable.

Some exemplary matrixes include swellable and non-swellable gels, elastomers, and rubbers. Swellable gels can include hydrogels and organogels. The term "hydrogel" indicates a cross-linked, water insoluble, water containing material. Hydrogels have many desirable properties for biomedical applications. For example, they can be made nontoxic and compatible with tissue, and they are usually highly permeable to water, ions and small molecules.

Gels generally comprise solid, cross-linked polymer networks capable of forming a stable system in equilibrium with an interpenetrating swelling agent. Many gel forming polymers are known in the art. Suitable gels include polymers, copolymers, and blockpolymers based on monomers containing ionizable groups or polymerizable double bonds. Exemplary monomers include, but are not limited to, acrylic acid, methyl methacrylate, methyl acrylic acid, ethyl acrylate, vinyl sulfonic acid, styrene, styrene sulfonic acid (e.g., p-styrene sulfonic acid), maleic acid, butenoic acid, vinyl phosphate, vinyl phosphonate, ethylene, propylene, styrene, vinyl methyl ether, vinyl acetate, vinyl alcohol, acrylonitrile, acrylamide, N—($C_1$-$C_6$ alkyl) acrylamide (such as N-isopropylacrylamide, N-t-butylacrylamide), and the like. Gels are made by homopolymerizing or copolymerizing any of the foregoing monomers. Other suitable gel materials can include, alginate, chitosan, collagen, gelatin, hyaluronate, fibrin, agarose, and derivatives thereof. The gel can be a copolymer as described above into which has been incorporated as one comonomeric component a ligand that connects to, complexes or physically entraps the desired magnetic material.

The gel can be cross-linked to let it take a physically stable form when hydrated or dehydrated. Suitable cross-linking can be provided by incorporating about 0.5 wt. % to about 1.5% wt. % of a cross-linking agent into the gel. Cross-linking can also be provided by incorporating about 0.01 mol % to about 15 mol % of the cross-linking agent in the gel.

Suitable crosslinking agents include compounds whose molecule has a plurality of reactive groups. Such molecular crosslinking agents may be N,N'-methylene-bis acrylamide or divinylbenzene (DVB), ethylene glycol dimethacrylate, divinyl ketone, vinyl methacrylate and divinyl oxalate. Ionic crosslinkage which uses ions such as metallic ions may also be employed. Crosslinkage using electromagnetic waves such as gamma rays is also possible. Cross-linking can also be based on electrostatic interactions, hydrogen boding, hydrophobic interactions or (micro)crystal formation.

Ionically cross-linkable polymers can be anionic or cationic in nature and include but not limited to carboxylic, sulfate, hydroxyl and amine functionalized polymers. The cross-linking ions used to crosslink the polymers can be anions or cations depending on whether the polymer is anionically or cationically cross-linkable. Appropriate cross-linking ions include but not limited to cations selected from the group consisting of calcium, magnesium, barium, strontium, boron, beryllium, aluminum, iron, copper, cobalt, lead and silver ions. Anions can be selected from but not limited to the group consisting of phosphate, citrate, borate, succinate, maleate, adipate and oxalate ions. More broadly, the anions are derived from polybasic organic or inorganic acids. Preferred cross-linking cations are calcium, iron, and barium ions. The most preferred cross-linking cations are calcium and barium ions. The most preferred cross-linking anion is phosphate. Cross-linking can be carried out by contacting the polymers with a nebulized droplet containing dissolved ions. One of ordinary skill in the art will be able to select appropriate cross-linking agent for the respective hydrogel used in the making of a multi-layer TE construct. For example, the gelation of collagen or alginate occurs in the presence of ionic cross-linker or divalent cations such as $Ca^{2+}$, $Ba^{2+}$ and $Sr^{2+}$.

In some embodiments, the gel comprises a biodegradable polymer selected from the group consisting of polyanhydrides, polyhydroxybutyric acid, polyorthoesters, polysiloxanes, polycaprolactone, poly(lactic-co-glycolic acid), poly(lactic acid), poly(glycolic acid), and copolymers prepared from the monomers of these polymers.

Suitable polymers which can be used in the present invention include but are not limited to one or a mixture of polymers selected from the group consisting of glycosaminoglycan, silk, fibrin, MATRIGEL®, poly-ethyleneglycol (PEG), polyhydroxy ethyl methacrylate, polyvinyl alcohol, polyacrylamide, poly (N-vinyl pyrolidone), poly glycolic acid (PGA), poly lactic-co-glycolic acid (PLGA), poly e-carpolactone (PCL), polyethylene oxide, poly propylene fumarate (PPF), poly acrylic acid (PAA), hydrolysed polyacrylonitrile, polymethacrylic acid, polyethylene amine, alginic acid, pectinic acid, carboxy methyl cellulose, hyaluronic acid, heparin, heparin sulfate, chitosan, carboxymethyl chitosan, chitin, pullulan, gellan, xanthan, collagen, gelatin, carboxymethyl starch, carboxymethyl dextran, chondroitin sulfate, cationic guar, cationic starch as well as salts and esters thereof. Polymers listed above which are not ionically cross-linkable are used in blends with polymers which are ionically cross-linkable. In some embodiments polymer is not gelatin.

Other preferred polymers include esters of alginic, pectinic or hyaluronic acid and C2 to C4 polyalkylene glycols, e.g. propylene glycol, as well as blends containing 1 to 99 wt % of alginic, pectinic or hyaluronic acid with 99 to 1 wt % polyacrylic acid, polymethacrylic acid or polyvinylalcohol. Preferred blends comprise alginic acid and polyvinylalcohol. Examples of mixtures include but are not limited to a blend of polyvinyl alcohol (PVA) and sodium alginate and propyleneglycol alginate.

In some embodiments, gel is alginate, collagen, or agarose.

As used herein, the term "magnetic material" refers to a material or substance that is influenced by a magnetic field, i.e. relative permeability ($\mu_r$) of the material is greater than unity. Such magnetic materials are intended to include those which are referred to as ferromagnetic, ferromagnetic, diamagnetic, paramagnetic, and superparamagnetic. As is the conventional understanding given that term, superparamagnetic materials exhibit magnetic properties only when in an externally applied magnetic field, and otherwise exhibit essentially no magnetic properties; and their total magnetism is greater than that of the individual particles considered separately. If the particle size of the magnetic material is sufficiently small, the magnetic material will most likely be superparamagnetic.

The magnetic properties of the composition are greatly influenced by the saturation magnetization, size, and concentration of magnetic material, as well as the strength of the external magnetic field.

The magnetic material can be any molecule, composition, particle, or substance, that exhibits magnetic properties when incorporated into the matrix. The magnetic materials can be selected from the group of elements having atomic numbers 21-29, 42, 44, and 57-70, elements having atomic numbers 24-29 or 62-69 being especially preferred. Preferably, a magnetic material is selected from the group including but not limited to, rare earth metals (such as gadolinium, terbium, dysprosium, holmium, erbium and europium), transient metals (such as iron, nickel, cobalt, magnesium chromium and copper), noble metals (such as rhodium, palladium), their oxides, compositions, combinations, solid dispersions, and alloys.

In some embodiments, the magnetic material is selected from the group consisting of maghemite ($Fe_2O_3$), magnetite ($Fe_3O_4$), strontium ferrite, samarium-cobalt, neodymium-iron-boron (NIB), lodestone, pyrrhotite, $BaFe_{12}O_{19}$, Alnico magnet alloy, transfer salts of decamethylmetallocenes with 7,7,8,8-tetracyano-p-quinodimethane (TCNQ) or tetracyanoethenide (TCNE) (such as $[Fe(Cp^*)_2]^+[TCNE]^-$, $[Fe(Cp^*)_2]^+$ $[TCNQ]^-$, $[Cr(Cp^*)_2]^+[TCNE]^-$, $[Cr(Cp^*)_2]^+[TCNQ]^-$, $[Mn(Cp^*)_2]^+[TCNE]^-$, and $[Mn(Cp^*)_2]^+[TCNQ]^-$), hexylammonium trichlorocuprate(II) ($CuCl_3(C_6H_{11}NH_3)$), Fe based amorphous magnetic powders, and combinations thereof. In some embodiments, the composition of the invention comprises two or more, e.g., two, three, four, five, different magnetic materials.

Exemplary Fe based amorphous magnetic powders are described in U.S. Pat. App. Pub. No. 2009/0232693, contents of which are herein incorporated by reference in their entirety.

In some embodiments, magnetic material is a particle, e.g. a magnetic nanoparticle, magnetic microparticle. Depending on the size, porosity or pore size of matrix, magnetic particles can rang in size from 1 nm to 1000 µms. Preferably magnetic particles are about 1 nm to 500 nm in size. In some embodiments, magnetic particle is a magnetic nano-particle of size about 300 nm. Magnetic nanoparticles are a class of nanoparticle which can be manipulated using magnetic field. Such particles commonly consist of magnetic elements such as iron, nickel and cobalt and their chemical compounds. Magnetic nano-particles are well known and methods described in the art, for example in U.S. Pat. Nos. 6,878,445; 5,543,158; 5,578,325; 6,676,729; 6,045,925 and 7,462,446, and U.S. Pat. Pub. Nos.: 2005/0025971; 2005/0200438; 2005/0201941; 2005/0271745; 2006/0228551; 2006/0233712; 2007/01666232 and 2007/0264199, contents of all of which are herein incorporated by reference in their entirety.

The magnetic material should be sufficiently immobilized in the matrix so that during any application of a magnetic field it cannot be removed therefrom by dissolution or chemical reaction that would be encountered, even as a result of a change in the porosity, pore size, pore connectivity, swelling agent concentration, and/or specific volume of the matrix. Thus, the magnetic material can be simply physically entrapped within the matrix, or it can be chemically bound into the matrix or complexed, encased in, or physically immobilized by an intermediate ligand which is in turn, chemically bound into the matrix. It is to be understood that physical immobilization includes chelation.

Compositions of the invention can be prepared using methods known in the art and easily adapted by one of skill in the art. For example, magnetic material can be bound to the matrix by carrying out the polymerization which forms the matrix in the presence of chelate-forming groups and then reacting this intermediate with an excess of the magnetic material in an aqueous solution. If desired, a bridging group, e.g. a linker, can be introduced between the chelate-forming groups and the matrix backbone, e.g. in a manner known per se.

Alternatively, the magnetic material can be present in cavities within the matrix, in the form of an insoluble or sparingly soluble substance or composition. The incorporation of the magnetic material within the matrix can be achieved in several ways.

In one method dry or incompletely swollen matrix may be swelled in an appropriate solution comprising a salt of a metal, for instance chloride and/or sulfate of said metal, whereafter the matrix is dried. The matrix is then swelled again in a solution, of a substance which is capable of precipitating the metal in the form of an insoluble or sparingly soluble magnetic material, compound or complex. For instance the precipitating substance may be a soluble phosphate, such as sodium phosphate, when the phosphate of the metal is insoluble or sparingly soluble in the medium in which the matrix is swelled. Alternatively, the precipitating substance may be an alkali metal hydroxide when the hydroxide of the metal is insoluble or sparingly soluble in the medium in which the matrix is swelled.

As used herein, the term "magnetic metal" refers to any metal that exhibits magnetic properties when it is incorporated in the matrix. The magnetic metal may or may not exhibit magnetic properties while it is not incorporated in the matrix. As used herein, magnetic metals includes ions, salts, oxides or nitrides of the metal.

According to another method, dry or incompletely swollen matrix material is swelled in a solution comprising a solvent in which the matrix material swells, e.g. water or dimethylsulfoxide, and one or more reagents of which at least one comprises the magnetic material in a suitable chemical form, and which reagents (optionally in contact with the matrix) produce by a chemical reaction (which may involve the matrix), for example a redox process, the magnetic material in elemental state or in the state of an insoluble or sparingly soluble chemical compound containing the magnetic material, said magnetic material being finely dispersed in the matrix.

According to another method the matrix is prepared by a process involving a cross-linking reaction carried out in a medium in which magnetic material or a complex thereof is dispersed, the magnetic material or complex being insoluble or sparingly soluble in said medium. Thus, the magnetic material or complex will become entrapped in a dispersed form in cavities formed in the three-dimensional network of the matrix. Where the magnetic material is incorporated as a complex, this is preferably a chelate complex which is insoluble or sparingly soluble in aqueous media.

Methods for preparing ferrogels have been described, for example, in Sahiner, N. Colloid Polym Sci (2006) 285: 283; Sauzeddle, F. Elaissari, A. and Picho, C. Colloid Polym Sci (1999) 277: 846; Gu, S. Shiratori, T. and Konno, M. Colloid Polym Sci (2003) 281: 1076; Zhang, J. et al., Adv Mater (2002) 14: 1756; and Caykara, T. Yörök, D. and Demirci, S. J App Polym Sci (2009) 112: 800, contents of all of which are herein incorporated by reference in their entirety.

Once matrix comprising magnetic material has been prepared, macropores can be introduced by freezing said matrix at temperature ranging from about −10° C. to about −180° C. and lyophilizing the matrix. In some embodiments, freezing temperature is about −15° C. to about −25° C. To prepare compositions comprising pores of size about 700 μm, a freezing temperature of about −20° C. is preferred. Lyophilized composition is then swelled in the appropriate swelling agent. Without wishing to be bound by theory, freezing temperature effects porosity and pore size of the resultant composition.

In some embodiments, the composition of the invention has an elastic modulus in the range between $10^{-3}$ and $10^3$ kPa. As used herein, the term "elastic modulus" refers to an object or substance's tendency to be deformed elastically (i.e., non-permanently) when a force is applied to it. Generally, the elastic modulus of an object is defined as the slope of its stress-strain curve in the elastic deformation region. Specifying how stress and strain are to be measured, including directions, allows for many types of elastic moduli to be defined. Young's modulus (E) describes tensile elasticity, or the tendency of an object to deform along an axis when opposing forces are applied along that axis; it is defined as the ratio of tensile stress to tensile strain. It is often referred to simply as the elastic modulus. The shear modulus or modulus of rigidity (G or μ) describes an object's tendency to shear (the deformation of shape at constant volume) when acted upon by opposing forces; it is defined as shear stress over shear strain. The shear modulus is part of the derivation of viscosity. The bulk modulus (K) describes volumetric elasticity, or the tendency of an object to deform in all directions when uniformly loaded in all directions; it is defined as volumetric stress over volumetric strain, and is the inverse of compressibility. The bulk modulus is an extension of Young's modulus to three dimensions. Three other elastic moduli are Poisson's ratio, Lamé's first parameter, and P-wave modulus.

In some embodiments, the compound is selected from the group consisting of small organic or inorganic molecules; saccharines; oligosaccharides; polysaccharides; peptides; proteins; peptide analogs and derivatives; peptidomimetics; nucleic acids; nucleic acid analogs and derivatives; an extract made from biological materials such as bacteria, plants, fungi, or animal cells; animal tissues; naturally occurring or synthetic compositions; and any combinations thereof.

In some embodiments, the composition further comprises a bioactive agent. As used herein, "bioactive agents" or "bioactive materials" refer to naturally occurring biological materials, for example, extracellular matrix materials such as fibronectin, vitronection, and laminin; cytokins; and growth factors and differentiation factors. "Bioactive agents" also refer to artificially synthesized materials, molecules or compounds that have a biological effect on a biological cell, tissue or organ.

Suitable growth factors and cytokines include, but are not limited, to stem cell factor (SCF), granulocyte-colony stimulating factor (G-CSF), granulocyte-macrophage stimulating factor (GM-CSF), stromal cell-derived factor-1, steel factor, VEGF, TGFβ, platelet derived growth factor (PDGF), angiopoeitins (Ang), epidermal growth factor (EGF), bFGF, HNF, NGF, bone morphogenic protein (BMP), fibroblast growth factor (FGF), hepatocye growth factor, insulin-like growth factor (IGF-1), interleukin (IL-)-3, IL-1α, IL-1β, IL-6, IL-7, IL-8, IL-11, and IL-13, colony-stimulating factors, thrombopoietin, erythropoietin, flt3-ligand, and tumor necrosis factor α (TNFα). Other examples are described in Dijke et al., "Growth Factors for Wound Healing", Bio/Technology, 7:793-798 (1989); Mulder G D, Haberer P A, Jeter K F, eds. Clinicians' Pocket Guide to Chronic Wound Repair. 4th ed. Springhouse, Pa.: Springhouse Corporation; 1998:85; Ziegler T. R., Pierce, G. F., and Herndon, D. N., 1997, International Symposium on Growth Factors and Wound Healing: Basic Science & Potential Clinical Applications (Boston, 1995, Serono Symposia USA), Publisher: Springer Verlag.

In some embodiments, suitable bioactive agents include but not limited to therapeutic agents. As used herein, the term "therapeutic agent" refers to a substance used in the diagnosis, treatment, or prevention of a disease. Any therapeutic agent known to those of ordinary skill in the art to be of benefit in the diagnosis, treatment or prevention of a disease is contemplated as a therapeutic agent in the context of the present invention. Therapeutic agents include pharmaceutically active compounds, hormones, growth factors, enzymes, DNA, plasmid DNA, RNA, siRNA, viruses, proteins, lipids, pro-inflammatory molecules, antibodies, antibiotics, anti-inflammatory agents, anti-sense nucleotides and transforming nucleic acids or combinations thereof. Any of the therapeutic agents may be combined to the extent such combination is biologically compatible.

Exemplary therapeutic agents include, but are not limited to, those found in *Harrison's Principles of Internal Medicine*, 13$^{th}$ Edition, Eds. T. R. Harrison et al. McGraw-Hill N.Y., N.Y.; Physicians Desk Reference, 50$^{th}$ Edition, 1997, Oradell N.J., Medical Economics Co.; Pharmacological Basis of Therapeutics, 8$^{th}$ Edition, Goodman and Gilman, 1990; United States Pharmacopeia, The National Formulary, USP XII NF XVII, 1990; current edition of Goodman and Oilman's *The Pharmacological Basis of Therapeutics*; and current edition of *The Merck Index*, the complete contents of all of which are incorporated herein by reference.

Examples of therapeutic agents which may be incorporated in the composition, include but are not limited to, narcotic analgesic drugs; salts of gold; corticosteroids; hormones; antimalarial drugs; indole derivatives; pharmaceuticals for arthritis treatment; antibiotics, including Tetracyclines, Penicillin, Streptomycin and Aureomycin; antihelmintic and canine distemper drugs, applied to domestic animals and large cattle, such, as, for example, phenothiazine; drugs based on sulfur, such, as sulfioxazole; antitumor drugs; pharmaceuticals supervising addictions, such as agents controlling alcohol addiction and agents controlling tobacco addiction; antagonists of drug addiction, such, as methadone; weight-controlling drugs; thyroid gland controlling drugs; analgesics; drugs controlling fertilization or contraception hormones; amphetamines; antihypertensive drugs; antiinflammatories agents; antitussives; sedatives; neuromuscular relaxants; antiepileptic drugs; antidepressants; antidisrhythmic drugs; vasodilating drugs; antihypertensive diuretics; antidiabetic agents; anticoagulants; antitubercu­lous agents; antipsyhotic agents; hormones and peptides. It is understood that above list is not full and simply represents the wide diversification of therapeutic agents that may be included in the compositions. In some embodiments, therapeutic agent is Mitoxantrone, protein (e.g. VEGF) or plasmid DNA.

The amount of therapeutic agent distributed in a composition depends on various factors including, for example, specific agent; function which it should carry out; required period of time for release of a the agent; quantity to be administered. Generally, dosage of a therapeutic agent i.e. amount of therapeutic agent in composition, is selected from the range about from 0.001% (w/w) up to 95% (w/w), preferably, from about 5% (w/w) to about 75% (w/w), and, most preferably, from about 10% (w/w) to about 60% (w/w).

In some embodiments, the composition comprises a cell, e.g. a biological cell. One way to incorporate cells into the composition is by reswelling a dried or partially dried composition of the invention in an aqueous solution comprising the cells to be incorporated. The aqueous solution can comprise from about $10^4$ to about $10^8$ cells/ml. In some embodiments, aqueous solution comprises from about $10^4$ to about $10^6$ cells/ml. In one preferred embodiment, aqueous solution comprises about $5\times10^5$ cells/ml.

In some embodiments, the composition comprises more that one cell type. This can be accomplished by having two or more different cell types in aqueous solution used for swelling. When two or more different cell types are to be incorporated into the composition, total number of cells in the aqueous solution ranges from about $10^4$ to about $10^8$ cells/ml, about $10^4$ to about $10^6$ cells/ml, or about $10^5$ cells/ml.

Cells amenable to be incorporated into the composition include, but are not limited to, stem cells (embryonic stem cells, mesenchymal stem cells, bone-marrow derived stem cells and hematopoietic stem cells), chrondrocytcs progenitor cells, pancreatic progenitor cells, myoblasts, fibroblasts, keratinocytes, neuronal cells, glial cells, astrocytes, pre-adipocytes, adipocytes, vascular endothelial cells, hair follicular stem cells, endothelial progenitor cells, mesenchymal cells, neural stem cells and smooth muscle progenitor cells.

In some embodiments, the cell is a genetically modified cell. A cell can be genetically modified to express and secrete a desired compound, e.g. a bioactive agent, a growth factor, differentiation factor, cytokines, and the like. Methods of genetically modifying cells for expressing and secreting compounds of interest are known in the art and easily adaptable by one of skill in the art.

Differentiated cells that have been reprogrammed into stem cells can also be used. For example, human skin cells reprogrammed into embryonic stem cells by the transduction of Oct3/4, Sox2, c-Myc and Klf4 (Junying Yu, et. al., 2007, Science 318: 1917-1920; Takahashi K. et. al., 2007, Cell 131: 1-12).

Cells useful for incorporation into the composition can come from any source, for example human, rat or mouse. Human cells include, but are not limited to, human cardiac myocytes-adult (HCMa), human dermal fibroblasts-fetal (HDF-f), human epidermal keratinocytes (HEK), human mesenchymal stem cells-bone marrow, human umbilical mesenchymal stem cells, human hair follicular inner root sheath cells, human umbilical vein endothelial cells (HU-VEC), and human umbilical vein smooth muscle cells (HU-VSMC), human endothelial progenitor cells, human myoblasts, human capillary endothelial cells, and human neural stem cells.

Exemplary rat and mouse cells include, but not limited to, RN-h (rat neurons-hippocampal), RN-c (rat neurons-cortical), RA (rat astrocytes), rat dorsal root ganglion cells, rat neuroprogenitor cells, mouse embryonic stein cells (mESC) mouse neural precursor cells, mouse pancreatic progenitor cells mouse mesenchymal cells and mouse endodermal cells.

In some embodiments, tissue culture cell lines can be used in the compositions described herein. Examples of cell lines include but are not limited to C166 cells (embryonic day 12 mouse yolk), C6 glioma Cell line, HL1 (cardiac muscle cell line), AML12 (nontransforming hepatocytes), HeLa cells (cervical cancer cell line) and Chinese Hamster Ovary cells (CHO cells).

An ordinary skill artisan in the art can locate, isolate and expand such cells. In addition, the basic principles of cell culture and methods of locating, isolation and expansion and preparing cells for tissue engineering are described in "Culture of Cells for Tissue Engineering" Editor(s): Gordana Vunjak-Novakovic, R. Ian Freshney, 2006 John Wiley & Sons, Inc., and in "Cells for tissue engineering" by Heath C. A. (Trends in Biotechnology, 2000, 18:17-19) and these are hereby incorporated by reference in their entirety.

The bioactive agent can be covalently linked to the matrix through a linker. The linker can be a cleavable linker or non-cleavable linker, depending on the application. As used herein, a "cleavable linker" refers to linkers that are capable of cleavage under various conditions. Conditions suitable for cleavage can include, but are not limited to, pH, UV irradiation, enzymatic activity, temperature, hydrolysis, elimination and substitution reactions, redox reactions, and thermodynamic properties of the linkage. In many cases, the intended nature of the conjugation or coupling interaction, or the desired biological effect, will determine the choice of linker group.

In some embodiments, the bioactive agent is bound to the matrix by a hydrolyzable bond. In some embodiments, the cell or the bioactive agent has a mean free path in the composition that is shorter than the mean free path of the cell or the bioactive agent in water.

A composition described herein can be administered to a subject by any appropriate route known in the art including, but not limited to, oral or parenteral routes, including intravenous, intramuscular, subcutaneous, transdermal, airway (aerosol), pulmonary, nasal, rectal, and topical (including buccal and sublingual) administration. As used herein, the term "administer" refers to the placement of a composition into a subject by a method or route which results in at least partial localization of the composition at a desired site such that desired effect is produced.

Exemplary modes of administration include, but are not limited to, injection, infusion, instillation, inhalation, or ingestion. "Injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. In some embodiments, the compositions are administered by intravenous infusion or injection.

For administration to a subject, composition comprising a bioactive agent can be formulated together with one or more pharmaceutically acceptable carriers (additives) and/or diluents. The pharmaceutical compositions of the present invention can be specially formulated for administration in solid or liquid form, including those adapted for the following: (1) oral administration, for example, drenches (aqueous or non-aqueous solutions or suspensions), lozenges, dragees, capsules, pills, tablets (e.g., those targeted for buccal, sublingual, and systemic absorption), boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; (8) transmucosally; or (9) nasally.

The composition comprising the bioactive agent can be delivered to an in vivo locus. Exemplary in vivo loci include, but are not limited to site of a wound, trauma or disease. The composition can be delivered to the in vivo locus by, for example, implanting the compositions into a subject.

Compositions that are to be implanted can additionally include one or more additives. Additives may be resolving (biodegradable) polymers, mannitol, starch sugar, inosite, sorbitol, glucose, lactose, saccharose, sodium chloride, calcium chloride, amino acids, magnesium chloride, citric acid, acetic acid, hydroxyl-butanedioic acid, phosphoric acid, glucuronic acid, gluconic acid, poly-sorbitol, sodium acetate, sodium citrate, sodium phosphate, zinc stearate, aluminium stearate, magnesium stearate, sodium carbonate, sodium bicarbonate, sodium hydroxide, polyvinylpyrolidones, polyethylene glycols, carboxymethyl celluloses, methyl celluloses, starch or their mixtures.

Implant can be of cylindrical form from about 0.5 to about 10 mm in diameter and from about 0.5 to about 10 cm in length. Preferably, its diameter is from about 1 to about 5 mm and length from about 1 to about 5 cm.

In some cases, implant can be of spherical form. When the implant is in a spherical form, its diameter can range from about 0.5 to about 50 mm in diameter. In some embodiments, a spherical implant's diameter is from about 5 to about 30 mm. Preferably the diameter is from about 10 to about 25 mm.

Controlled Drug Release

In another aspect, the invention provides a on-demand method for controlling the release of a bioactive agent, the method comprising: (a) providing or administering to a subject a composition described herein, wherein the composition contains the bioactive agent; and (b) inducing a change in porosity, pore size, pore connectivity, swelling agent concentration, and/or specific volume of the composition via a magnetic field to control the release of the bioactive agent. As used herein, the term "on-demand" refers to the operator control over the release of bioactive agent from the composition.

Release of the bioactive agent can be achieved in a pulsalite manner by repeated application of external stimuli. This ability for on-demand pulsatile release of bioactive agents is useful in a variety of settings, including immunizations, which typically provide an initial immunization, followed by distinct booster doses at later times. Moreover, repeated administration of well-defined doses of allergen, in the absence of immunostimulatory molecules, from such a polymer matrix may be useful for inducing tolerance. It also may be advantageous to use an external stimuli to deliver bioactive agents in a pulsatile manner so as to time the delivery to coincide with a particular biological event (e.g. the circadian rhythm) in order to maximize the effectiveness of the bioactive agent (e.g. against tumors).

In some cases, the composition can release the bioactive agent continuously, and application of a stimuli allows release to of the bioactive agent to be decreased or stopped in emergent clinical situations. For example, an implantable composition can be designed to hold a chemotherapeutic therapeutic agent. Without the presence of an applied magnetic field, the therapeutic agent will continuously disperse out from the composition, however, in the presence of an applied magnetic field, rate of dispersion will be lowered. This can be useful, for example, when there is a need to hold chemotherapeutic therapeutic agents with immunodepressant side-effects while treating infections.

Other Applications of Macroporous Gels

Due to its large deformation, fast response, reversible motion and biocompatiblility, the magnetic gels can be used in a physiological environment as a bioactuator. For example, it may be used as a magnetic field controlled artificial muscle.

A significant amount of solvent flows into/out of the magnetic gel during its deformation. Therefore, one may use magnetic field to drive the magnetic gel to act as a pump in microfluidic chips. Further, the reversible deformation of the magnetic gel may also be used as valves in microfluidic chips to open or close microfluidic channels.

Deformation sensitive pigments may also be added into the magnetic gel (Lu Y. F. et al., Nature (2001), 410:19). A magnetic field induces the deformation of the gel, as well as the pigments encapsulated in it. Therefore, the pigments may change color or florescence in response to magnetic field.

Owing to fast response times and substantial specific volume changes in response to an external stimuli, compositions described herein can be employed for numerous applications, particularly in medicine, pharmaceutics, drug-delivery, biosensors, bio-actuators, optical devices, valves and pumps for microfluidics, separation and membranes, purifications, and enzyme and cell immobilization. See for example, Qiu, Y. and Park, K. Adv Drug Delivery Rev (2001), 53: 321-339; Miyata, T. Urgami, T. and Nakamae, K. Adv. Drug Delivery Rev. (2002), 54: 79-98; Bckiari, V. et al., Langmuir (2004), 20: 7972; Lopes, D. Cendoya, L. and Mijangos, C. Macromol Symp (2001), 166:173; Lao, L. and Ramanujan, V. R. J Mater Sci Mater Med (2004), 15: 1061; Porter, J. and Pickup, R. W. J. Microbiol. Methods (1998), 33: 221; Xie, X. et al., J Magn Mater (2004), 227: 16 and Gupta, P. K. and Hung, C. T. Life Sci (19889) 44, 175.

DEFINITIONS

Unless otherwise defined herein, scientific and technical terms used in connection with the present application shall have the meanings that are commonly understood by those of ordinary skill in the art. Further, unless otherwise required by context, singular terms shall include pluralities and plural terms shall include the singular.

As used herein the term "comprising" or "comprises" is used in reference to compositions, methods, and respective component(s) thereof, that are essential to the invention, yet open to the inclusion of unspecified elements, whether essential or not.

As used herein the term "consisting essentially of" refers to those elements required for a given embodiment. The term permits the presence of additional elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

Other than in the operating examples, or where otherwise indicated, all numbers expressing quantities of ingredients or reaction conditions used herein should be understood as modified in all instances by the term "about." The term "about" when used in connection with percentages may mean±1%. Furthermore, the term "about" can mean within ±1% of a value.

The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description.

Although methods and materials similar or equivalent to those described herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example."

The terms "decrease", "reduced", "reduction", "decrease" or "inhibit" are all used herein generally to mean a decrease by a statistically significant amount. However, for avoidance of doubt, "reduced", "reduction" or "decrease" or "inhibit" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (e.g. absent level as compared to a reference sample), or any decrease between 10-100% as compared to a reference level.

The terms "increased", "increase" or "enhance" or "activate" are all used herein to generally mean an increase by a statically significant amount; for the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

The term "statistically significant" or "significantly" refers to statistical significance and generally means a two standard deviation (2SD) above or below a reference level. The term refers to statistical evidence that there is a difference. It is defined as the probability of making a decision to reject the null hypothesis when the null hypothesis is actually true. The decision is often made using the p-value.

By "treatment", "prevention" or "amelioration" of a disease or disorder is meant delaying or preventing the onset of such a disease or disorder, reversing, alleviating, ameliorating, inhibiting, slowing clown or stopping the progression, aggravation or deterioration the progression or severity of a condition associated with such a disease or disorder. In one embodiment, the symptoms of a disease or disorder are alleviated by at least 5%, at least 10%, at least 20%, at least 30%, at least 40%, or at least 50%.

As used here, the term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used here, the term "pharmaceutically-acceptable carrier" means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) $C_2$-$C_{12}$ alchols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein.

As used herein, the term "polymer" is intended to include both oligomeric and polymeric species, i.e., compounds which include two or more monomeric units, which may be a homopolymer or a copolymer. The term "homopolymer" is a polymer incorporating a single species of monomer units. The term "copolymer" is a polymer constructed from two or more chemically distinct species of monomer units in the same polymer chain. A "block copolymer" is a polymer which incorporates two or more segments of two or more distinct species of homopolymers or copolymers.

As used herein, the term "swelling agent" refers to those compounds or substances which affect at least a degree of swelling. Typically, swelling agents is an aqueous solution or organic solvent, however swelling agent can also be a gas. In some embodiments, swelling agent is water or a physiological solution, e.g. phosphate buffer saline, or growth media As used herein, the term "linker" means an organic moiety that connects two parts of a compound. Linkers typically comprise a direct bond or an atom such as oxygen or sulfur, a unit such as SS, NH, C(O), C(O)NH, SO, $SO_2$, $SO_2$NH or a chain of atoms, such as substituted or unsubstituted alkyl where one or more methylenes can be interrupted or terminated by O, S, S(O), $SO_2$, NH, $NH_2$, C(O).

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. Patient or subject includes any subset of the foregoing, e.g., all of the above, but excluding one or more groups or species such as humans, primates or rodents. In certain embodiments, the subject is a mammal, e.g., a primate, e.g., a human. The terms, "patient" and "subject" are used interchangeably herein.

Preferably, the subject is a mammal. The mammal can be a human, non-human primate, mouse, rat, dog, cat, horse, or cow, but are not limited to these examples. Mammals other than humans can be advantageously used as subjects that represent animal models of HIF or hypoxia related pathologies. In addition, the methods described herein can be used to treat domesticated animals and/or pets. A subject can be male or female. A subject can be one who has been previously diagnosed with or identified as suffering from or having a HIF or hypoxia related pathology, one or more complications related to a HIF or hypoxia related pathology, and optionally, but need not have already undergone treatment for such a HIF or hypoxia related pathology.

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

To the extent not already indicated, it will be understood by those of ordinary skill in the art that any one of the various embodiments herein described and illustrated may be further modified to incorporate features shown in any of the other embodiments disclosed herein.

The present invention can be defined in any of the following numbered paragraphs:

1. A composition comprising a matrix material and a magnetic material distributed therethrough, wherein the composition comprises pores having mean pore diameter in range of about 100 μm to about 1000 μm, and wherein porosity, pore size, pore connectivity, swelling agent concentration and/or specific volume of the composition undergoes a change from a first value to a second value in response to an electromagnetic signal.
2. The composition of paragraph 1, wherein the composition comprises 0.1%-50% of matrix material, 1-90% of magnetic material.
3. The composition of any of paragraphs 1-2, wherein the composition comprises a swelling agent.
4. The composition of any of paragraph 1-3, wherein the composition comprises 0.1-50% of matrix material, 1-90% of magnetic material and a swelling agent in an amount corresponding to the balance up to 100%.
5. The composition of any of paragraphs 1-4, wherein the composition comprises ~1% of matrix material, ~13% magnetic material, and ~86% of a swelling agent, by weight.
6. The composition of any of paragraphs 1-5, wherein the composition comprises pores having mean pore diameter in range of about 200 μm to about 1000 μm.
7. The composition of any of paragraphs 1-6, wherein the composition comprises pores having mean pore diameter of 700 μm.
8. The composition of any of paragraphs 1-7, wherein the composition has porosity of 0.1 to 0.99.
9. The composition of any of paragraphs 1-8, wherein the composition has porosity of at least 0.9.
10. The composition of any of paragraphs 1-9, wherein the matrix material is a polymer, copolymer, or blockpolymer gel.
11. The composition of any of paragraphs 1-10, wherein the matrix material is a cross-linked polymer, copolymer, or blockpolymer gel.
12. The composition of paragraph 11, wherein the matrix comprises 0.01 mol % to 15 mol % of a cross-linking agent.
13. The composition of any of paragraphs 1-12, wherein the matrix material comprises a monomer selected from the group consisting of acrylic acid, methyl methacrylate, methyl acrylic acid, ethyl acrylate, vinyl sulfonic acid, styrene, styrene sulfonic acid (e.g., p-styrene sulfonic acid), maleic acid, butenoic acid, vinyl phosphate, vinyl phosphonate, ethylene, propylene, styrene, vinyl methyl ether, vinyl acetate, vinyl alcohol, acrylonitrile, acrylamide, N—($C_1$-$C_6$ alkyl) acrylamide (such as N-isopropylacrylamide, N-t-butylacrylamide), and combinations thereof.
14. The composition of any of paragraphs 1-13, wherein the matrix material comprises a polymer selected from the group consisting of glycosaminoglycan, silk, fibrin, MATRIGEL®, poly-ethyleneglycol (PEG), polyhydroxy ethyl methacrylate, polyvinyl alcohol, polyacrylamide, poly (N-vinyl pyrolidone), poly(lactic acid), poly glycolic acid (PGA), poly lactic-co-glycolic acid (PLGA), poly e-carpolactone (PCL), polyethylene oxide, poly propylene fumarate (PPF), poly acrylic acid (PAA), polyhydroxybutyric acid, hydrolysed polyacrylonitrile, polymethacrylic acid, polyethylene amine, esters of alginic acid; pectinic acid; and alginate, hyaluronic acid, carboxy methyl cellulose, heparin, heparin sulfate, chitosan, carboxymethyl chitosan, chitin, pullulan, gellan, xanthan, collagen, gelatin, carboxymethyl starch, carboxymethyl dextran, chondroitin sulfate, cationic guar, cationic starch, and combinations thereof.
15. The composition of any of paragraphs 1-14, wherein the magnetic material is ferromagnetic, ferromagnetic, diamagnetic, paramagnetic, or superparamagnetic.
16. The composition of any of paragraphs 1-15, wherein the magnetic material is selected from group rare earth metals, transient metals, noble metals, and oxides, compositions, combinations, solid dispersions, and alloys thereof.
17. The composition of any of paragraphs 1-16, wherein the magnetic material is selected from the group consisting of maghemite ($Fe_2O_3$), magnetite ($Fe_3O_4$), strontium ferrite, samarium-cobalt, neodymium-iron-boron (NIB), lodestone, pyrrhotite, $BaFe_{12}O_{19}$, Alnico magnet alloy, transfer salts of decamethylmetallocenes with 7,7,8,8-tetracyano-p-quinodimethane (TCNQ) or tetracyanoethenide (TCNE) (such as $[Fe(Cp^*)_2]^+[TCNE]^-$, $[Fe(Cp^*)_2]^+[TCNQ]^-$, $[Cr(Cp^*)_2]^+[TCNE]^-$, $[Cr(Cp^*)_2]^+[TCNQ]^-$, $[Mn(Cp^*)_2]^+[TCNE]^-$, and $[Mn(Cp^*)_2]^+[TCNQ]^-$), hexylammonium trichlorocuprate(II) ($CuCl_3(C_6H_{11}NH_3)$, Fe based amorphous magnetic powders, and combinations thereof.
18. The composition of any of paragraph 1-17, wherein the magnetic material is a magnetic particle having a size from about 1 nm to 1000 μm.
19. The composition of any of paragraphs 1-18, wherein the magnetic material is a magnetic nano-particle.
20. The composition of any of paragraphs 1-19 wherein the composition comprises a bioactive agent.
21. The composition of paragraph 20, wherein the bioactive agent is covalently linked to the matrix.
22. The composition of paragraphs 20 or 21, wherein the bioactive agent is a therapeutic agent.
23. The composition of any of paragraphs 1-22, wherein the composition comprises a cell.
24. The composition of paragraph 23, wherein the cell is a human cell, mouse cell or rat cell.
25. The composition of any of paragraphs 1-24, wherein porosity, pore size, pore connectivity, swelling agent concentration, and/or specific volume changes by at least 10%, 15%, 20%, 25% 30%, 40%, 50%, 60%, 70%, 80%, 90%, 95%, 96%, 97%, 98%, 99% or more relative to the original value on application of a magnetic field.

26. The composition of any of paragraphs 1-25, wherein porosity, pore size, pore connectivity, swelling agent concentration, and/or specific volume decreases on application of a magnetic field.
27. The composition of any of paragraphs 1-26, wherein the electromagnetic signal has a defined magnetic field strength
28. The composition of paragraph 27, wherein the magnetic field strength is from about 0.001 Tesla to about 1 Tesla.
29. A method for preparing the composition of any of paragraphs 1-28, method comprising: (a) preparing a composition comprising a magnetic material; (b) freezing the composition of step (a), wherein freezing temperature is from about −4° C. to about −170° C.; (c) lyophilizing the frozen composition; (d) swelling the lyophilized composition.
30. The method of paragraph 29, wherein freezing temperature is from about −10° C. to about −25° C.
31. The method of any of paragraphs 29 or 30, wherein freezing temperature is about −20° C.
32. A method for controlling the release of a bioactive agent, the method comprising: (a) providing to a subject a composition of any of paragraphs 1-31, wherein the composition comprises the bioactive agent; and (b) inducing a change in porosity, pore size, pore connectivity, swelling agent concentration, and/or specific volume of the composition via a magnetic field to control the release of the bioactive agent.

The following examples illustrate some embodiments and aspects of the invention. It will be apparent to those skilled in the relevant art that various modifications, additions, substitutions, and the like can be performed without altering the spirit or scope of the invention, and such modifications and variations are encompassed within the scope of the invention as defined in the claims which follow. The following examples do not in any way limit the invention.

EXAMPLES

Example 1

Preparation of Macroporous Magnetic Gels $FeCl_2.4H_2O$, $FeCl_3.6H_2O$ and $NH_4OH$ were used to prepare magnetite particles by the chemical co-precipitation method as described in Betancourt-Galindo et al, J. Magn. Magn. Mater. (2005), 294: 33. The average diameter of the magnetite particles obtained was ~300 nm. The magnetite particles were further coated with polymers such as poly (acrylamide-co-acrylichydrazide) with molecular weight ~1500 Dalton. The coated magnetite particles were mixed with alginate solution. The resulted alginate solution was immediately crosslinked with adipic acid dihydrazide to form a magnetic alginate hydrogel according to the method described in F. Bueche, F. and Halpin, J. C., Journal of Applied Physics (1964), 35:36. The weight ratio of magnetic nanoparticle, polymer, and water in the final solution was 13%, 1%, and 86%, respectively.

Magnetite particle comprising gels were frozen at temperature raging from −20° C. to −180° C. (e.g., at −20° C., −80° C., and −180° C.), and then lyophilized. The freeze-lyophilize process introduced macropores with diameters ranging from 700 μm to 300 μm into the gels. Table 1 lists average pore diameter formed at various temperatures.

TABLE 1

| Average pore diameters. | |
|---|---|
| Freeze temperature (° C.) | Average pore diameter |
| −20 | 700 μm |
| −80 | 200 μm |
| −180 | 10 μm |

Figure 1:
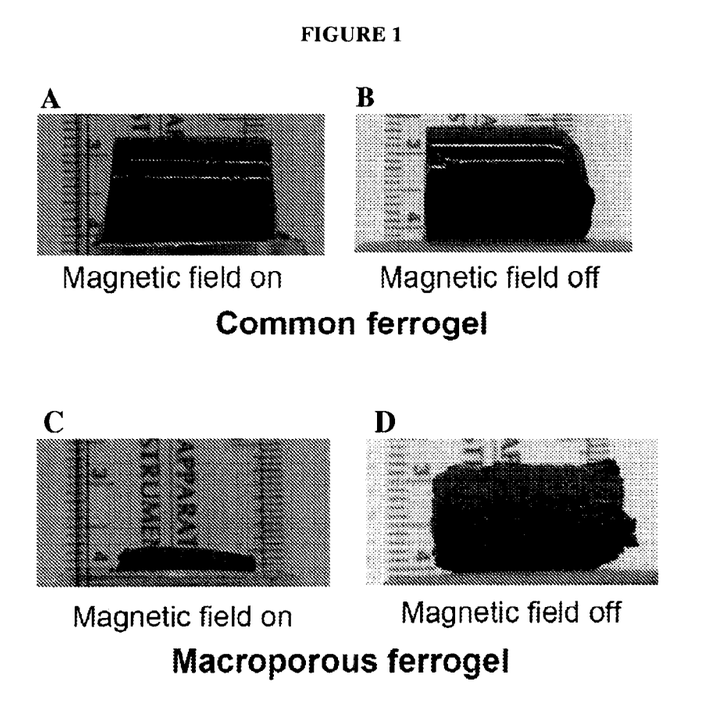
FIGS. 1A-1D are photographs showing much larger deformation (~83% compressive strain) and volume variation (~90% volume reduced) of macroporous gels (FIGS. 1C and 1D) of the invention in comparison to the small deformation (~5% compressive strain) and almost no volume change of the ferrogels currently available (FIGS. 1A and 1B) under the same magnetic field.

The macroporous gels were re-swollen in de-ionized water. The weight concentration of polymer, magnetite particles and water was ~1%, ~13%, and ~86% in the final macroporous gel. FIG. 1 shows change in specific volume of a magnetic gel described herein (FIGS. 1C and 1D) in comparison to a common ferrogel having a similar composition but average pore diameter of less than 100 nm (FIGS. 1A and 1B). As can be seen in FIG. 1, magnetic gel of the invention undergoes a volume change of about 75%; in comparison there is little change in specific volume of common ferrogel.

Example 2

Controlled Release of Mitoxantrone

Figure 2:
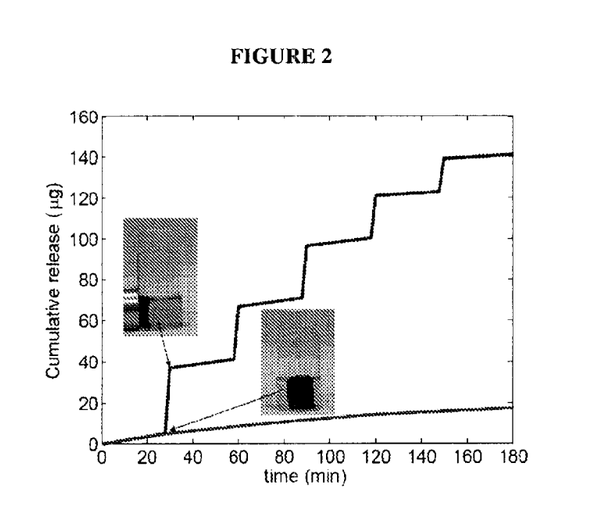
FIG. 2 is a line graph showing that deformation of macroporous ferrogel is reversible, and the response time to magnetic field is less than 1 s. The convection of physiological fluids out of the pores of the ferrogel greatly enhances the release of drugs (e.g. Mitoxantrone) previously encapsulated in the gel matix.

The lyophilized magnetic gels were soaked in 150 μg/ml Mitoxantrone solution for 6 hours. Since Mitoxantrone is positively charged and alginate is negatively charged, they tend to interact with each other to enable the encapsulation of Mitoxantrone in the gel matrix. Thereafter, the Mitoxantrone-loaded gels were placed in Dulbecco's Modified Eagle Medium A magnetic field having field strength about 0.5 Tesla was turned on for 2 minutes and then turned off every 30 minutes for 3 hours. The magnetic field deformed the gel, and released encapsulated Mitoxantrone into solution. As shown in FIG. 2, when no magnetic field was applied the gel released Mitoxantrone by diffusion (red curve, lower curve), but when a magnetic field was applied the gel released Mitoxantrone by convection (blue curve, upper curve).

Example 3

Controlled Release of Cells

Figure 3:
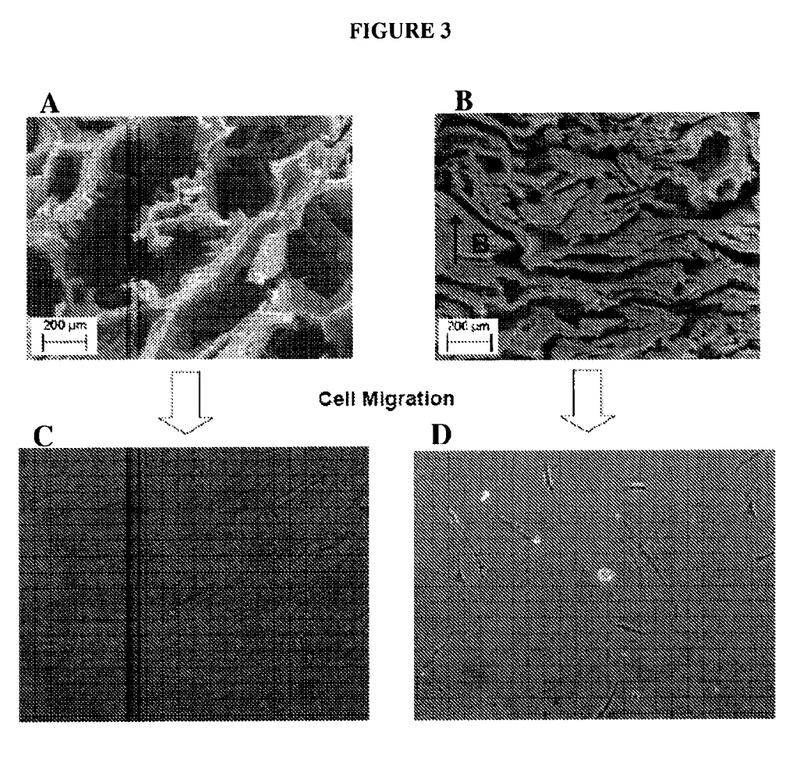

The lyophilized magnetic gels were soaked in $10^5$ per mL of cell (fibroblast cells) suspension solution for 6 hours for cell engraftment. Thereafter, cell-loaded gels were placed in petri dishes for cell migration study. A magnetic field of strength about 0.5 Tesla was applied to the gels. Application of the magnetic field deformed the pores (with diameter ~700 μm) into slits (with height ~30 μm). For the control case, no magnetic field was applied. As shown in FIG. 3, on application of the magnetic filed, the reduced pore size greatly retarded cell migration out of the gel.

The invention claimed is:
1. A composition comprising a matrix material and a magnetic material distributed therethrough, wherein the composition comprises macropores having mean pore diameter in range of about 100 μm to about 1000 μm, wherein the magnetic material is in form of magnetic particles having a size in the range from about 1 nm to about 500 nm, and wherein porosity, pore size, pore connectivity, swelling agent concentration and/or specific volume of the composition changes by at least 10% in response to an electromagnetic signal.
2. The composition of claim 1, wherein the composition comprises a swelling agent.
3. The composition of claim 1, wherein the composition has porosity of 0.1 to 0.99.

4. The composition of claim 1, wherein the matrix material is a polymer, copolymer, or blockpolymer gel.

5. The composition of claim 4, wherein the matrix material is a cross-linked polymer, copolymer, or blockpolymer gel.

6. The composition of claim 1, wherein the matrix material comprises a polymer selected from the group consisting of glycosaminoglycan, silk, fibrin, MATRIGEL®, poly-ethyleneglycol (PEG), polyhydroxy ethyl methacrylate, polyvinyl alcohol, polyacrylamide, poly (N-vinyl pyrolidone), poly (lactic acid), poly glycolic acid (PGA), poly lactic-co-glycolic acid (PLGA), poly e-carpolactone (PCL), polyethylene oxide, poly propylene fumarate (PPF), poly acrylic acid (PAA), polyhydroxybutyric acid, hydrolysed polyacrylonitrile, polymethacrylic acid, polyethylene amine, esters of alginic acid; pectinic acid; and alginate, fully or partillay oxidized alginate, hyaluronic acid, carboxy methyl cellulose, heparin, heparin sulfate, chitosan, carboxymethyl chitosan, chitin, pullulan, gellan, xanthan, collagen, gelatin, carboxymethyl starch, carboxymethyl dextran, chondroitin sulfate, cationic guar, cationic starch, and combinations thereof.

7. The composition of claim 1, wherein the magnetic material is ferromagnetic, ferromagnetic, diamagnetic, paramagnetic, or superparamagnetic.

8. The composition of claim 1, wherein the macropores have a mean pore diameter in range of about 150 µm to about 750 µm.

9. The composition of claim 1, wherein the composition comprises a bioactive agent.

10. The composition of claim 9, wherein the bioactive agent is mitoxantrone.

11. The composition of claim 9, wherein the bioactive agent is covalently linked to the matrix.

12. The composition of claim 9, wherein the bioactive agent is a therapeutic agent.

13. The composition of claim 1, wherein the composition comprises a cell.

14. The composition of claim 1, wherein porosity, pore size, pore connectivity, swelling agent concentration, and/or specific volume changes by at least 25% or more relative to the original value on application of a magnetic field.

15. The composition of claim 1, wherein porosity, pore size, pore connectivity, swelling agent concentration, and/or specific volume decreases on application of a magnetic field.

16. The composition of claim 1, wherein the matrix material comprises a cell binding molecule.

17. The composition of claim 1, wherein the magnetic material is distributed homogeneously within the matrix material.

18. The composition of claim 1, wherein the composition comprises a compound selected from the group consisting of small organic or inorganic molecules; saccharines; oligosaccharides; polysaccharides; peptides; proteins; peptidomimetics; nucleic acids; an extract made from biological materials and any combinations thereof.

19. The method of claim 18, wherein the biological materials is bacteria, plants, fungi, animal cells or animal tissues.

20. The method of claim 18, wherein the composition comprises animal tissues; naturally occurring or synthetic compositions; and any combinations thereof.

21. The composition of claim 18, wherein the compound is covalently linked to the matrix.

22. A method for preparing the composition of claim 1, method comprising: (a) preparing a composition comprising a magnetic material; (b) freezing the composition of step (a), wherein freezing temperature is from about −4° C. to about −180° C.; (c) lyophilizing the frozen composition; (d) swelling the lyophilized composition.

23. A method for controlling the release of a bioactive agent, the method comprising: (a) providing to a subject a composition of claim 1, wherein the composition comprises the bioactive agent; and (b) inducing a change in porosity, pore size, pore connectivity, swelling agent concentration, and/or specific volume of the composition via a magnetic field to control the release of the bioactive agent.

* * * * *

UNITED STATES PATENT AND TRADEMARK OFFICE
CERTIFICATE OF CORRECTION

PATENT NO. : 9,089,512 B2
APPLICATION NO. : 13/516973
DATED : July 28, 2015
INVENTOR(S) : David J. Mooney et al.

It is certified that error appears in the above-identified patent and that said Letters Patent is hereby corrected as shown below:

In the Specification

At Column 1, Line numbers 18-22, delete "The invention was made with government support under grant no. DMR-0820484 awarded by the National Science Foundation and under grant no. DE013033 awarded by the national Institutes of Health. The government has certain rights in this invention." and replace it with -- This invention was made with government support under DE019917, and DE013033 awarded by the National Institutes of Health, and 0820484 awarded by the National Science Foundation. The government has certain rights in the invention. --

Signed and Sealed this
Twenty-third Day of April, 2024

Katherine Kelly Vidal
*Director of the United States Patent and Trademark Office*